United States Patent
Woo et al.

(10) Patent No.: US 6,596,230 B1
(45) Date of Patent: Jul. 22, 2003

(54) DEVICE AND METHOD FOR PATHOGEN INACTIVATION OF THERAPEUTIC FLUIDS WITH STERILIZING RADIATION

(75) Inventors: Lecon Woo, Libertyville, IL (US); Daniel R. Boggs, Lake Bluff, IL (US); Shmuel Sternberg, Palatine, IL (US); Craig Sandford, Wheeling, IL (US); Atul Khare, Crystal Lake, IL (US); Julian Breillatt, Mundelein, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/494,338

(22) Filed: Jan. 28, 2000

(51) Int. Cl.[7] .............................. A61L 2/08; A61L 2/10
(52) U.S. Cl. ............................ 422/22; 422/44; 422/24; 250/433
(58) Field of Search ................... 422/24, 44; 250/435, 250/437, 438, 455.11, 433, 22

(56) References Cited

U.S. PATENT DOCUMENTS

| | | | |
|---|---|---|---|
| 5,133,932 A | 7/1992 | Gunn et al. | 422/24 |
| 5,290,221 A | 3/1994 | Wolf, Jr. et al. | 604/4 |
| 5,300,019 A | 4/1994 | Bischof et al. | 604/4 |

(List continued on next page.)

FOREIGN PATENT DOCUMENTS

| | | |
|---|---|---|
| AU | 42470/85 A | 11/1986 |
| AU | 70408/91 B | 5/1992 |
| DE | 3500385 A1 | 9/1986 |

(List continued on next page.)

OTHER PUBLICATIONS

John Rudge, Carol McLean, Shirley MacDonald, Tony Jones, Ian Cameron, Ron McIntosh, and Duncan Pepper, Poster Presentation: Validation of a Continuous Flow Device for UV–C Virus Inactivation Process at Production Scale, XVIIth Congress of The International Society on Thrombosis And Haemostasis—Washington DC, Aug. 14–21, 1999.

Sing Chin, Bolanle Williams, Paul Gottlieb, Henrietta Margolis–Nunno, Ehud Ben–Hur, John Hamman, Rongyu Jin, Edward Dubovi, and Bernard Horowitz, Virucidal Short Wavelength Ultraviolet Light Treatment of Plasma and Factor VIII Concentrate: Protection of Proteins by Antioxidants, *Blood*, vol. 86, No. 11, Dec. 1, 1995, pp. 4331–4336.

*Primary Examiner*—Elizabeth McKane
(74) *Attorney, Agent, or Firm*—Joseph A. Fuchs

(57) ABSTRACT

A device and method for inactivating pathogens in therapeutic fluids with sterilizing radiation in a continuous thin fluid flow arrangement that exhibits radiation dose uniformity for fluids having high optical densities. Radiation dose uniformity is achieved in part through a "carrying" mechanism that moves or carries the fluid, thereby eliminating a channel flow velocity profile where flow volumes near the channel walls run the risk of overexposure to the radiation due to very large residence times within the channel. The device comprises a relatively flat belt chamber (22) connected to a fluid flow through an inlet (24) and an outlet (26) on the belt chamber (22). The belt chamber (22) has a top surface (28) and a bottom surface (30). A radiation permeable plate (32) is disposed adjacent the top surface (28) of the belt chamber (22) and is in contact with the belt chamber (22). A radiation source (42) is provided adjacent to the plate (32) adjacent to a side opposite the belt chamber (22). A belt (34) having a plurality of flexible vanes (36) is disposed adjacent the bottom surface (30) of the belt chamber (22) such that the vanes (36) make contact with the belt chamber (22). The belt is driven by a roller mechanism (38) in the direction of the fluid flow. As the fluid flows through the belt chamber (22), the flexible vanes (36) provide a squeegee-like mechanism to move the fluid through the belt chamber (22) in discrete packets (40) defined by a pair of vanes (36). As the packets of fluid move through the belt chamber, they are exposed to sterilizing radiation passing through the plate (32).

27 Claims, 5 Drawing Sheets

U.S. PATENT DOCUMENTS

| | | | |
|---|---|---|---|
| 5,364,645 A | 11/1994 | Lagunas-Solar et al. | 426/248 |
| 5,418,167 A | 5/1995 | Matner et al. | 435/288 |
| 5,567,616 A * | 10/1996 | Dill, II | 422/24 X |
| 5,607,711 A | 3/1997 | Lagunas-Solar | 426/248 |
| 5,683,661 A | 11/1997 | Hearst et al. | 422/186.3 |
| 5,770,147 A | 6/1998 | Mueller | 422/24 |
| 5,854,967 A | 12/1998 | Hearst et al. | 422/186.3 |
| 5,972,593 A | 10/1999 | Wollowitz et al. | 435/2 |
| 6,369,394 B1 * | 4/2002 | Lee | 422/25 X |

FOREIGN PATENT DOCUMENTS

| | | |
|---|---|---|
| EP | 0201650 A1 | 11/1986 |
| EP | 0525138 B1 | 2/1993 |
| EP | 0 422 007 B1 | 10/1995 |
| JP | 61 263690 A | 11/1986 |
| JP | 7155177 A | 6/1995 |
| JP | 7327674 A | 12/1995 |
| JP | 8038167 A | 2/1996 |
| JP | 8224080 A | 9/1996 |
| JP | 3 51996 B2 | 6/2000 |
| WO | WO92/11060 A1 | 7/1992 |
| WO | WO 97/02058 A1 | 1/1997 |
| WO | WO97/46271 A1 | 12/1997 |
| WO | WO 97/46846 A1 | 12/1997 |

* cited by examiner

DEVICE AND METHOD FOR PATHOGEN INACTIVATION OF THERAPEUTIC FLUIDS WITH STERILIZING RADIATION

TECHNICAL FIELD

The present invention relates to the treatment of biological fluids with sterilizing radiation to inactivate various pathogens, such as viruses, in human plasma. In particular, the present invention relates to a device and method for inactivating pathogens with sterilizing radiation in a continuous flow arrangement while exhibiting radiation dose uniformity.

BACKGROUND OF THE INVENTION

In the transfusion and infusion medicine field, beneficial fluids are introduced to a patient for therapeutic purposes. Many of these fluids are of biologic origin, such as blood, plasma, or various fractions of blood or plasma. For example, blood plasma protein Factor VIII, which promotes blood coagulation to prevent life threatening bleeding, is used for maintaining hemostasis for hemophilic patients who lack the Factor VIII. Another example is plasma-derived immunoglobulin, which is used for strengthening and supplementing a patient's immune defense. Contamination of such fluids with donor blood borne pathogens, such as viruses and other microorganisms, can be detrimental to the patient's health and may even result in death of the patient. Therefore, methods must be set in place to substantially eliminate these pathogens before these fluids are introduced to the patient while minimizing the denaturation of useful fluid components during the pathogen inactivation process.

Existing methods for pathogen inactivation include detergent treatment for inactivating lipid-enveloped viruses, thermal treatment, and chemical and photochemical treatment for rendering various viral agents innocuous. Some of the photochemical treatment methods are described in U.S. Pat. Nos. 5,683,661, 5,854,967, 5,972,593, and the references cited therein. However, these methods tend to be less conducive to high volume and continuous processing applications, such as a production line for the manufacture of Factor VIII or immunoglobulin. These methods are also expensive.

Sterilizing radiation in the form of short ultraviolet (UV) wavelengths, gamma radiation or electron beam (beta) radiation has been found to be effective for inactivation of a broad range of pathogens. The use of a sterilizing radiation process is typically more economical than chemical treatments. Sterilizing radiation is defined as electromagnetic radiation capable of rupturing bonds in the genetic nucleaic acids (DNA) of pathogens. Nucleaic acids are typically much more susceptible to damage by sterilizing radiation than the protein products treated.

U.S. Pat. No. 5,133,932 describes an apparatus for batch treatment of biological fluids with ultraviolet radiation. However, the batch processing method disclosed causes irradiation of the fluids in a spatially uneven manner. Furthermore, the random and chaotic agitation process disclosed causes broad exposure time for various fluid components. This uneven exposure may cause inconsistent radiation dosage, which may result in ineffective pathogen removal (underexposure) or damage to beneficial biological agents (overexposure).

A continuous flow process for the irradiation of biological fluids is more effective than batch processing and is more conducive to high volume production. In a continuous flow process involving a constant sterilizing radiation illumination field, the transit time, or residence time, of the fluid is directly related to the radiation dose received by the fluid. Therefore, a continuous flow treatment process requires that the residence time distribution of the fluid being exposed to the radiation be as uniform as possible. By analogy with the batch process, short residence time distributions lead to an insufficient inactivation dose of radiation and long residence time distributions could lead to damage and reduced potency of beneficial biological agents.

Present continuous flow methods involve fluid flow in a channel. A parabolic velocity profile exists for such fluid flow. In this profile, the fluid at the center of the channel is traveling at maximum velocity and the fluid close to the channel wall remains nearly stationary. Therefore, the residence time is the shortest for the maximum velocity at the center and increases for successive portions of the flow profile moving radially outwardly from the center. In the absence of turbulence or mechanical agitation, the flow volume near the channel walls would have an extremely long residence time. Thus, the flow volume near the channel walls runs the risk of overexposure to the radiation. In addition, if the particular channel wall is on the proximal side of the radiation source, very serious overexposure of the biological fluid can occur.

In addition to residence time distribution, the penetration depth of sterilizing radiation into various biological fluids is also a factor in controlling consistent radiation dosage of the fluid. Depending on the optical density of a particular biological fluid, the penetration of sterilizing radiation into the fluid can be very shallow. This is especially true in the case of low or moderate energy accelerated electrons or short wavelength UV radiation. For example, the penetration of 200 Kev electrons into water is less than 0.5 mm (20 mils). Similarly, UV radiation at 250 nm wavelength loses half of the intensity in human plasma at about a 75 micron (about 3 mils) penetration. Thus, a thin fluid flow path can be advantageous in providing a more uniform radiation dosage to the fluid.

International Application No. PCT/GB97/01454 describes a UV irradiation apparatus that utilizes a static mixer disposed within a cylindrical fluid passage to facilitate mixing of the fluid. The apparatus also incorporates a heat exchanger to control the fluid temperature and prevent localized heating during irradiation. The localized heating purportedly causes the formation of insoluble particles of material. These particles may screen pathogens from the UV radiation, and, therefore, the '01454 patent application provides a heat exchanger to reduce the likelihood that these particles will form. However, this apparatus focuses on the control of fluid temperature rather than control of residence time distribution of the fluid. The presence of the static mixer increases the flow resistance and has a significant adverse effect on the residence time distribution of the fluid and also significantly increases the pressure head of the fluid flow, thereby making this device less conducive to high volume throughput. Furthermore, the deep channels formed between the screw elements is conducive to non-uniform radiation dosage of the fluid despite the mixing of the fluid. This apparatus does not provide a controlled method for dealing with non-uniform dose exposure due to shallow penetration depth.

These shortcomings in the prior art have created a need for providing a more controlled method for uniform radiation exposure in continuous flow arrangements, particularly for fluids having high optical densities.

It is therefore an object of the present invention to provide a continuous flow device and method that is highly effective in uniformly irradiating high optical density fluids having low radiation penetrations.

It is also an object of the present invention to provide a continuous flow device and method for pathogen inactivation of biological fluids with sterilizing radiation utilizing a thin fluid flow path that promotes a more uniform radiation exposure for fluids having high optical densities.

It is also an object of the present invention to provide a continuous flow device and method utilizing a thin fluid flow path while providing a uniform and narrow residence time distribution of the fluid within the device, thereby providing yet another control over radiation exposure.

It is another object of the present invention to substantially eliminate the development of a velocity profile of the fluid flowing through the device by incorporating a "conveying" mechanism to move the fluid through the device in a controlled manner.

It is another object of the present invention to provide a continuous flow device and method having a minimal air/fluid interface, thereby minimizing protein degradation in the fluid.

It is another object of the present invention to a continuous flow device and method capable of thin film fluid manipulation while minimizing shear stress and shear induced degradation of high protein fluid products.

It is another object of the present invention to provide a continuous flow device and method that is scalable and therefore capable of high volume throughput that is conducive to manufacturing production lines.

It is another object of the present invention to provide a continuous flow device and method that is economical and cost effective.

It is another object of the present invention to provide a continuous flow device and method that is adaptable to various different radiation sources.

It is another object of the present invention to provide a continuous flow device and method that allows for ease of cleaning or provides a disposable fluid path.

It is another object of the present invention to provide a continuous flow device and method that is capable of validation, i.e., demonstration of efficacy, reproducibility and reliability through scientific principles.

These and other objects will be readily apparent after reviewing the description and drawings herein.

SUMMARY OF THE INVENTION

The present invention is a device and method for inactivating pathogens in biological fluids with sterilizing radiation in a continuous and thin fluid flow path that exhibits radiation dose uniformity and narrow residence time distribution of the fluid within the device.

In a first embodiment, a thin film fluid path is provided through a thin and relatively flat fluid chamber arrangement. In this device, a relatively flat belt chamber is connected to a fluid flow through an inlet on one end of the belt chamber and an outlet on the other end of the belt chamber. The belt chamber is designed to be disposable. An external pump or other means provides a fluid supply to the device. The belt chamber has a first relatively flat surface and a second relatively flat surface. A radiation permeable plate is disposed adjacent one surface of the belt chamber and is in contact with the belt chamber. A radiation source is provided adjacent a side of the plate opposite the belt chamber. The radiation source provides sterilizing radiation at the optimal wavelengths for the particular fluid. A belt having a plurality of flexible vanes is disposed adjacent the other surface of the belt chamber such that the vanes make contact with the belt chamber. The belt is driven by a roller mechanism in the direction of the fluid flow. As the fluid is introduced into the belt chamber, the flexible vanes provide a squeegee-like action to move the fluid through the belt chamber in discrete packets defined by a pair of vanes. A tension adjuster can be provided to adjust the pressure of the vanes against the belt chamber and plate. As the packets of fluid move through the belt chamber, they are exposed to radiation passing through the high transparency plate.

In a variation of the previously described embodiment, the belt having the flexible vanes is replaced with a belt having a plurality of rotating rigid cylinders. The belt is similarly disposed adjacent the belt chamber such that the cylinders make contact with the belt chamber. The belt is driven by a roller mechanism in the direction of the fluid flow. In this embodiment, as the belt moves the rotation of the rigid cylinders provides a squeegee-like action to move the fluid through the belt chamber in discrete packets defined by a pair of cylinders. A tension adjuster can be provided to adjust the pressure of the rigid cylinders against the belt chamber and the plate. As the packets of fluid move through the belt chamber, they are exposed to radiation passing through the plate.

In another embodiment, a series of rollers having flexible vanes spirally disposed thereon are disposed adjacent to a surface of the belt chamber. The rollers are synchronously driven by a motor and drive mechanism. As the rollers rotate, the spiral vanes push the fluid through the belt chamber. A tension adjuster can be provided to adjust the pressure of the vanes against the belt chamber and plate. As the fluid moves through the belt chamber, they are exposed to radiation passing through the plate.

In yet another embodiment, a narrow belt chamber is positioned parallel to a large roller having a plurality of flexible vanes spirally disposed thereon. The roller is disposed adjacent to and in contact with one surface of the belt chamber and a high transparency plate is disposed adjacent and in contact with the other surface of the belt chamber. A radiation source is provided on a side of the plate opposite the belt chamber. In this configuration, the fluid is moved along through the belt chamber by the spirally configured flexible vanes. The fluid is exposed to radiation passing through the plate as the fluid moves through the belt chamber.

In yet another embodiment, an inner cylinder is concentrically disposed within a hollow radiation permeable outer cylinder having an outer surface and an inner surface. A radiation source is provided around the outside surface of the outer cylinder. A motor rotatably drives the inner cylinder. The inner cylinder has a plurality of flexible vanes angled in a direction opposite that of the direction of rotation. A flexible and relatively flat belt chamber having a fluid inlet and a fluid outlet is disposed between, and in contact with, the inner surface of the outer cylinder and the inner cylinder. A pump provides a fluid supply to the belt chamber. As the fluid is introduced into the belt chamber, the inner cylinder rotates and the flexible vanes provide a squeegee-like action to move the fluid through the belt chamber in discrete packets defined by a pair of vanes. As the packets of fluid move through the belt chamber, they are exposed to radiation passing through the outer cylinder.

In another embodiment, a stationary elongated V-shaped depositor is disposed within a rotating hollow radiation permeable cylinder having an inner surface and an outer surface. A motor rotatably drives the cylinder. A fluid inlet is in fluid communication with the depositor. The depositor deposits a thin film of fluid on the inner surface of the cylinder as the cylinder rotates. The thin film is carried on the inner surface of the cylinder until it reaches a stationary squeegee collector in contact with the inner surface of the cylinder. A radiation source is provided around the outside surface of the cylinder and irradiates the thin film of fluid carried on the inner surface of the cylinder. The squeegee collector is in fluid communication with a fluid outlet. The irradiated fluid exits the device through the fluid outlet. One or more pumps provide a fluid supply to the fluid inlet and from the fluid outlet.

DETAILED DESCRIPTION OF THE INVENTION

While the present invention will be described fully hereinafter with reference to the accompanying drawings, in which a particular embodiment is shown, it is to be understood at the outset that persons skilled in the art may modify the invention herein described while still achieving the desired result of this invention. Accordingly, the description which follows is to be understood as a broad informative disclosure directed to persons skilled in the appropriate arts and not as limitations of the present invention.

Figure 1:
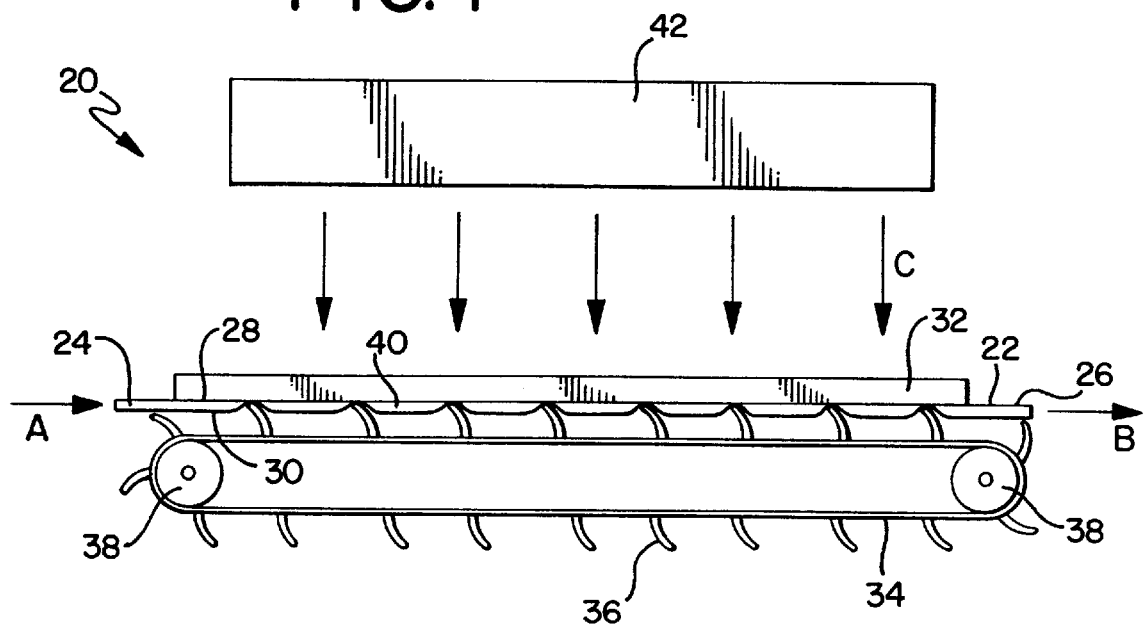
FIG. 1 is a side elevational view of a first embodiment of the present invention that utilizes a belt mechanism having flexible vanes to move a fluid through a chamber being exposed to sterilizing radiation.
Figure 2:
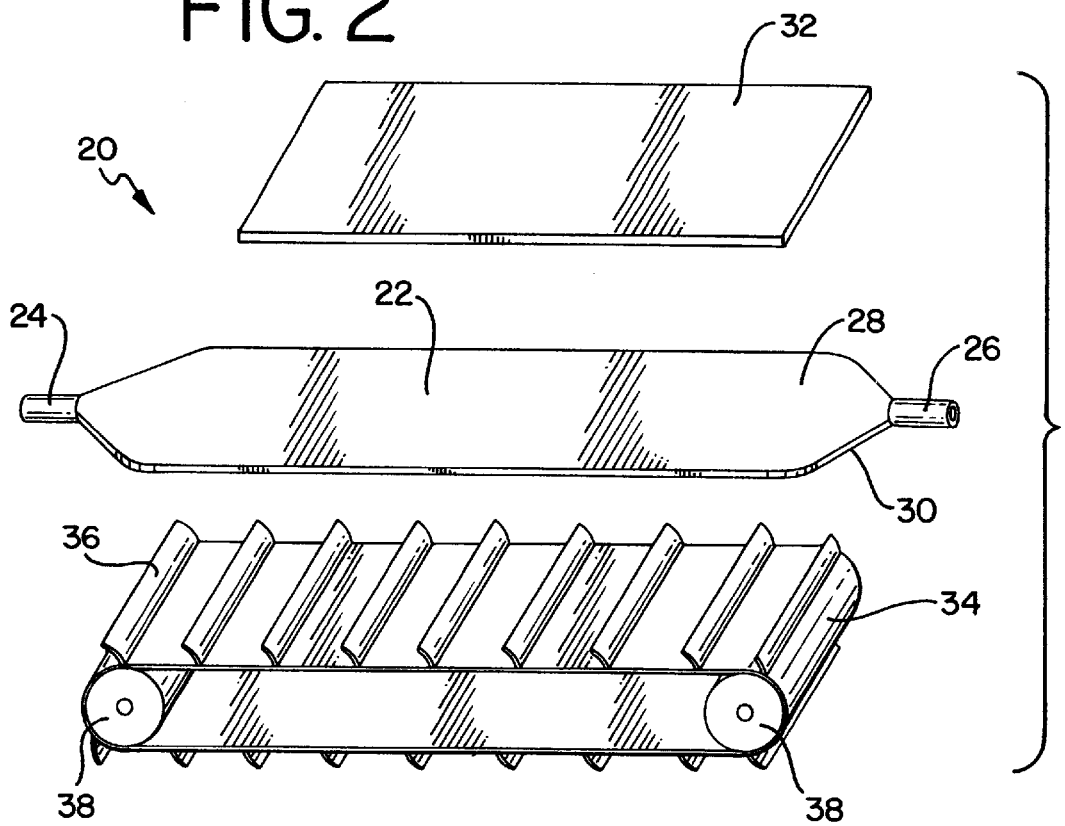
FIG. 2 is an assembly view of the basic elements of the first embodiment depicted in FIG. 1.

A thin film fluid irradiation device 20 is shown in FIGS. 1 and 2. In this device, a relatively flat belt chamber 22 is connected to a fluid flow, indicated by arrows A and B in FIG. 1, via a fluid inlet 24 at one end of the belt chamber 22 and a fluid outlet 26 at the other end of the belt chamber 22. A pump (not shown) or other means delivers a fluid supply to the belt chamber 22. The belt chamber 22 has a top surface 28 and a bottom surface 30. Preferably, the belt chamber 22 is designed to be disposable. A radiation permeable form, in the form of a plate 32, is disposed on the top surface 28 of the belt chamber 22 and is in contact with the belt chamber 22. The plate 32 is highly transparent to the particular radiation utilized to sterilize the fluid. Preferably, the plate 32 is made from fused quartz or poly (methylpentene). A belt 34 having a plurality of flexible vanes 36 is disposed adjacent the bottom surface 30 of the belt chamber 22 such that the vanes 36 make contact with the belt chamber 22. The contact pressure of the vanes 36 against the bottom surface 30 of the belt chamber 22 and the plate 32 can be adjusted with a tension adjuster (not shown), which adjusts the relative position of the belt 34 with respect to the plate 32. The belt 34 is driven in the direction of the fluid flow by a roller mechanism 38 mechanically connected to a motor (not shown). The flexible vanes 36 of the belt 34 are preferably angled in a direction toward the fluid inlet 24.

As the fluid is introduced into the belt chamber 22, the flexible vanes 36 provide a squeegee-like action against the belt chamber 22 and the plate 32 and move the fluid through the belt chamber 22 in discrete packets 40 defined by a pair of adjacent vanes 36, as shown in FIG. 1. This squeegee-like action helps eliminate or minimize the formation of a typical fluid flow velocity profile within the belt chamber, and, therefore, eliminates or minimizes the effects that channel flow velocity profiles have on residence times of the fluid.

A radiation source 42 is generically depicted in FIG. 1. The radiation source 42 provides sterilizing radiation (indicated by arrows C in FIG. 1) to the plate 32. As the fluid is moved through the belt chamber 22, the fluid is exposed to sterilizing radiation passing through the plate 32. The belt chamber 22 is dimensioned to provide a thin fluid path. The dimensions of the thin fluid path are primarily defined by consideration of the optical density of the particular fluid being sterilized and the effective penetration of the sterilizing radiation into the fluid. The required fluid volume throughput of the device is also a consideration.

Figure 3:
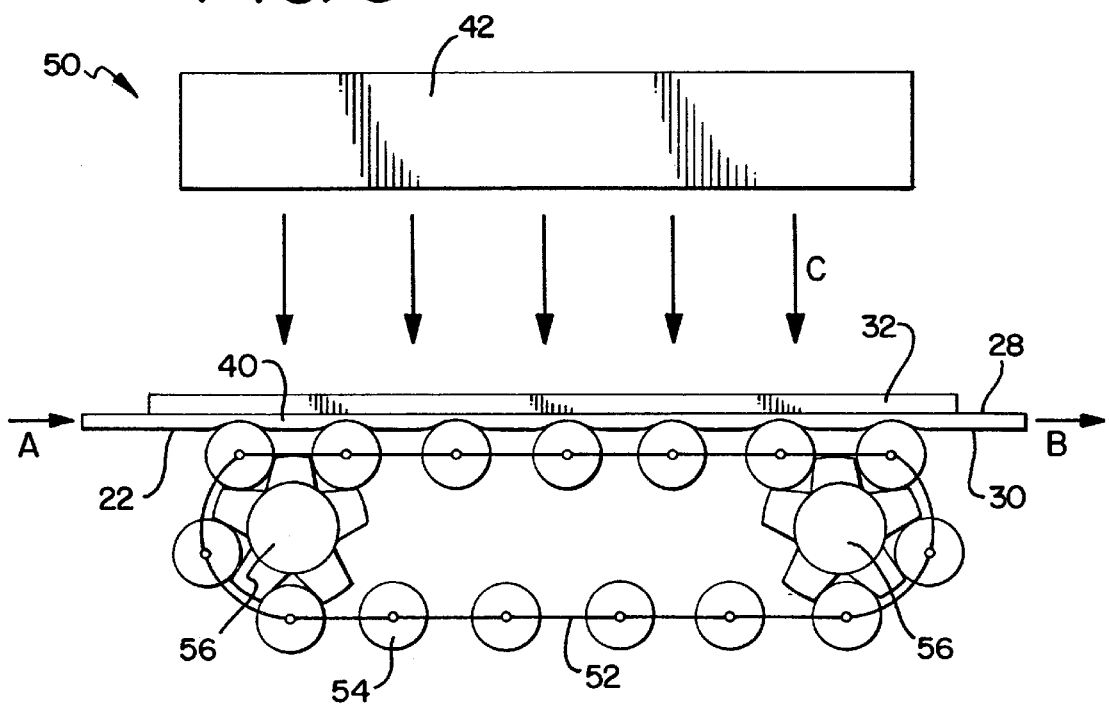
FIG. 3 is a side elevational view of a second embodiment of the present invention that utilizes a belt mechanism having rotating rigid cylinders to move a fluid through a chamber being exposed to sterilizing radiation.
Figure 4:
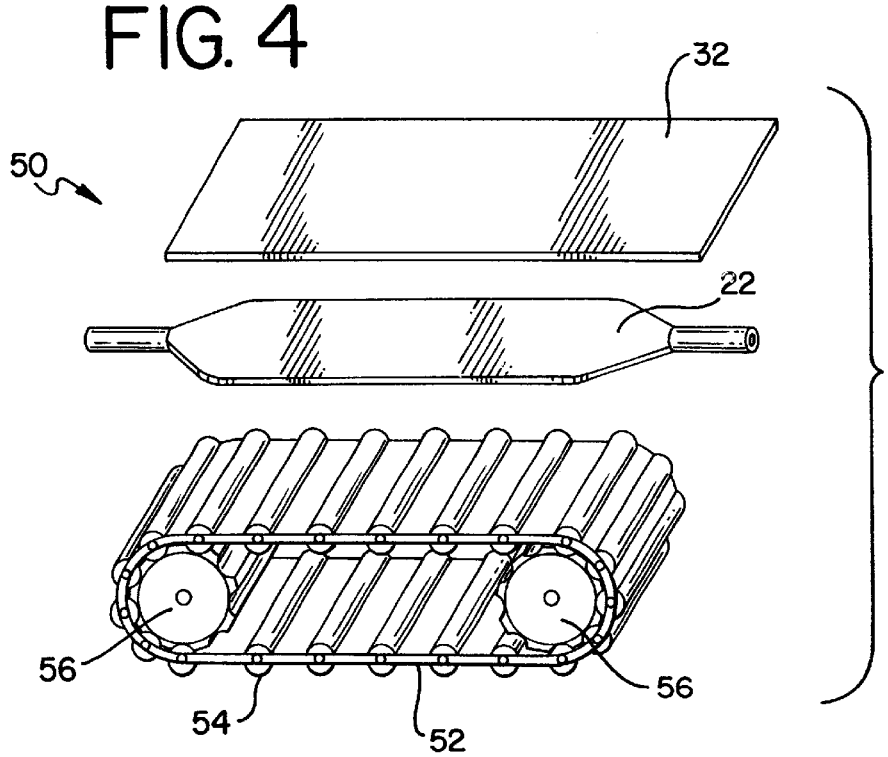
FIG. 4 is an assembly view of the basic elements of the second embodiment depicted in FIG. 3.

FIGS. 3 and 4 show an alternate embodiment device indicated by 50. The device 50 is substantially similar to the device 20, except that device 50 incorporates a belt 52 having a plurality of rotatable rigid cylinders 54. The belt 52 is disposed adjacent to the bottom surface 30 of the belt chamber 22. Thus, the rigid cylinders 54 are used in place of the flexible vanes 36 of the device 20 shown in FIGS. 1 and 2.

The belt 52 is positioned such that the cylinders 54 make contact with the bottom surface 30 of the belt chamber 22. The plate 32 is disposed on the top surface 28 of the belt chamber 22 and is in contact with the belt chamber 22. The contact pressure of the cylinders 54 against the bottom surface 30 of the belt chamber 22 and the plate 32 can be adjusted with a tension adjuster (not shown), which adjusts the relative position of the belt 34 with respect to the plate 32. The belt 52 is driven in the direction of the fluid flow (indicated by arrows A and B in FIG. 3) by a roller mechanism 56 that is mechanically connected to a motor (not shown).

In this embodiment, as the belt 52 moves with respect to the belt chamber 22, the rotation of the rigid cylinders 54 provides the squeegee-like action to move the fluid through the belt chamber 22 in discrete packets 40 defined by an adjacent pair of cylinders 54. The generically depicted radiation source 42 provides sterilizing radiation (indicated by arrows C in FIG. 3) to the plate 32. The fluid is exposed to sterilizing radiation passing through the plate 32 as the fluid moves through the belt chamber 22.

Figure 5:
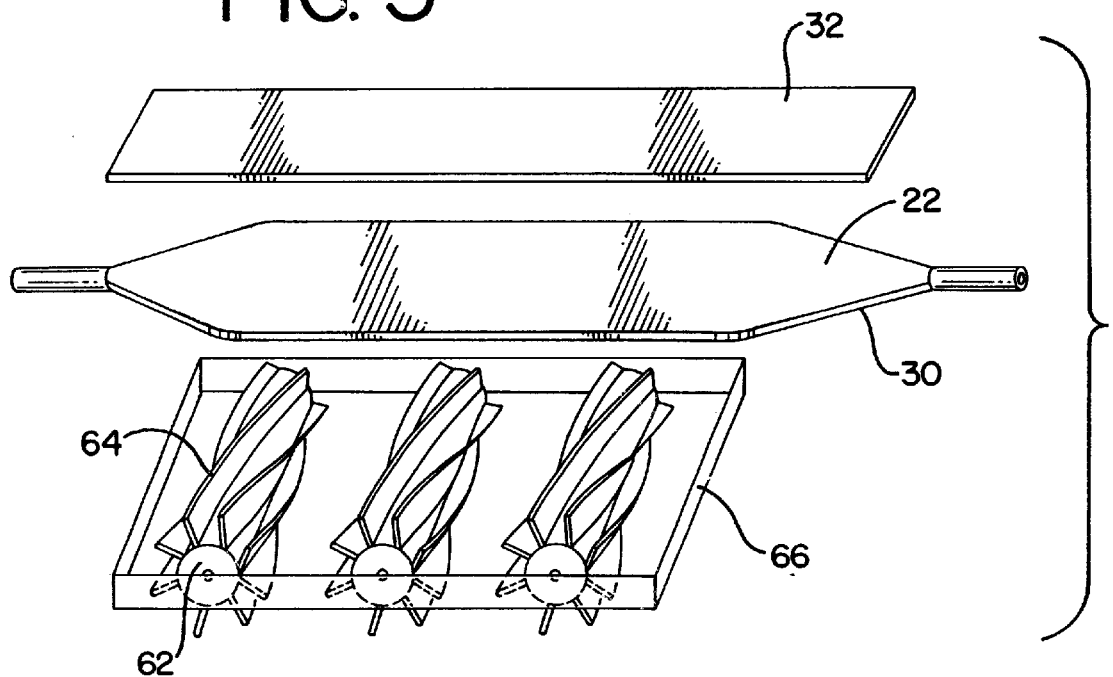
FIG. 5 is an assembly view of the basic elements of a third embodiment of the present invention that utilizes a series of rollers having spirally configured flexible vanes to move a fluid through a chamber being exposed to sterilizing radiation.

In yet another embodiment, the belt 52 of device 50 is replaced with a series of individual rollers 62 having a plurality of flexible vanes 64 spirally disposed thereon. The main elements of this embodiment are shown in FIG. 5. The rollers 62 are disposed adjacent to the bottom surface 30 of the belt chamber 22. The rollers 62 are held in a position that is transverse to the fluid flow by a frame 66 and are synchronously driven by a motor (not shown) and drive mechanism (not shown). As the rollers 62 rotate, the spiral vanes 64 push the fluid through the belt chamber 22. A tension adjuster (not shown) is used to adjust the pressure of the spiral vanes 64 against the belt chamber 22 and the plate 32. As in the previously described embodiments, the fluid is exposed to sterilizing radiation passing through the plate 32 as the fluid moves through the belt chamber 22.

Figure 6:
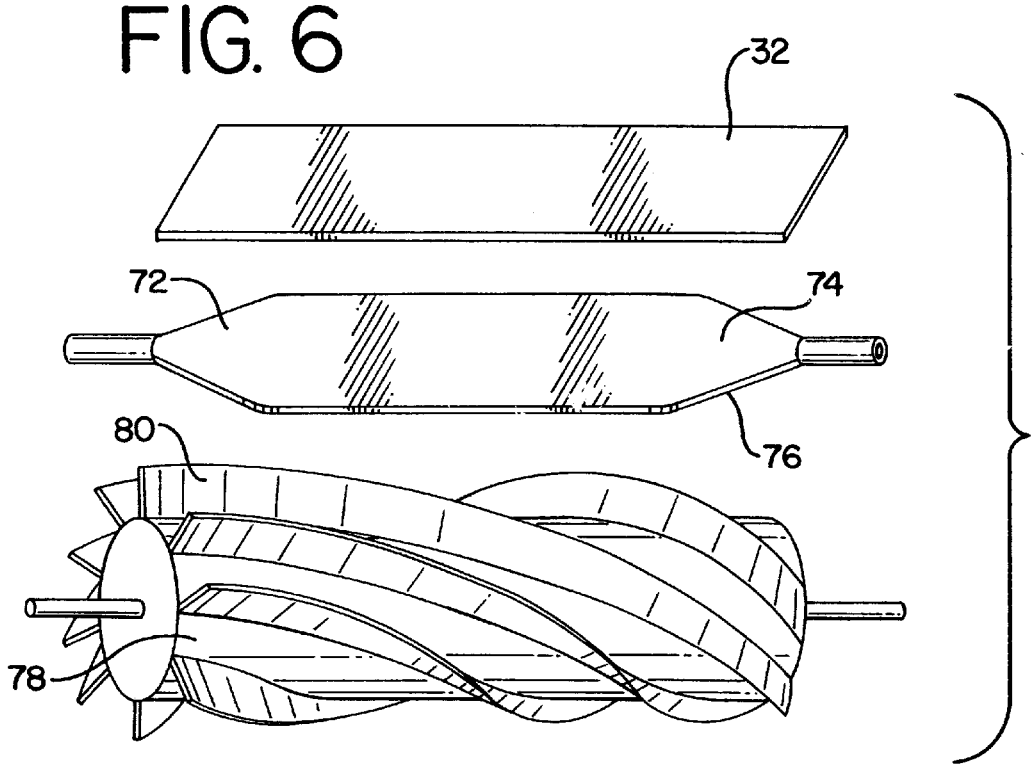
FIG. 6 is an assembly view of the basic elements of a fourth embodiment of the present invention that utilizes a single roller having spirally configured flexible vanes positioned parallel to a thin chamber being exposed to sterilizing radiation to move a fluid through the chamber.

The main elements of yet another embodiment based on the concept of device 50 are shown in FIG. 6. In this embodiment, a narrow belt chamber 72 is utilized, which is narrower than the belt chamber 22. Preferably, the belt chamber 72 is designed to be disposable. The narrow belt chamber 72 has a top surface 74 and a bottom surface 76 and is positioned parallel to a large roller 78 having a plurality of flexible vanes 80 spirally disposed thereon. The roller 78 is disposed adjacent to and in contact with the bottom surface 76 of the narrow belt chamber 72. The plate 32 is disposed adjacent and in contact with the top surface 74 of the belt chamber 72. The roller is driven by a motor (not shown) and drive mechanism (not shown).

In this configuration, the fluid is moved along through the belt chamber 72 by a screw-like linear action of the spirally configured vanes 80 as the roller 78 rotates. This embodiment utilizes the narrow belt chamber 72 so that the vanes 80 of the single roller 78 can effectively make contact with the belt chamber 72 across substantially the entire width of the belt chamber 72. Similar to the previously described embodiments, the fluid is exposed to sterilizing radiation passing through the plate 32 as the fluid moves through the belt chamber 72.

Figure 7:
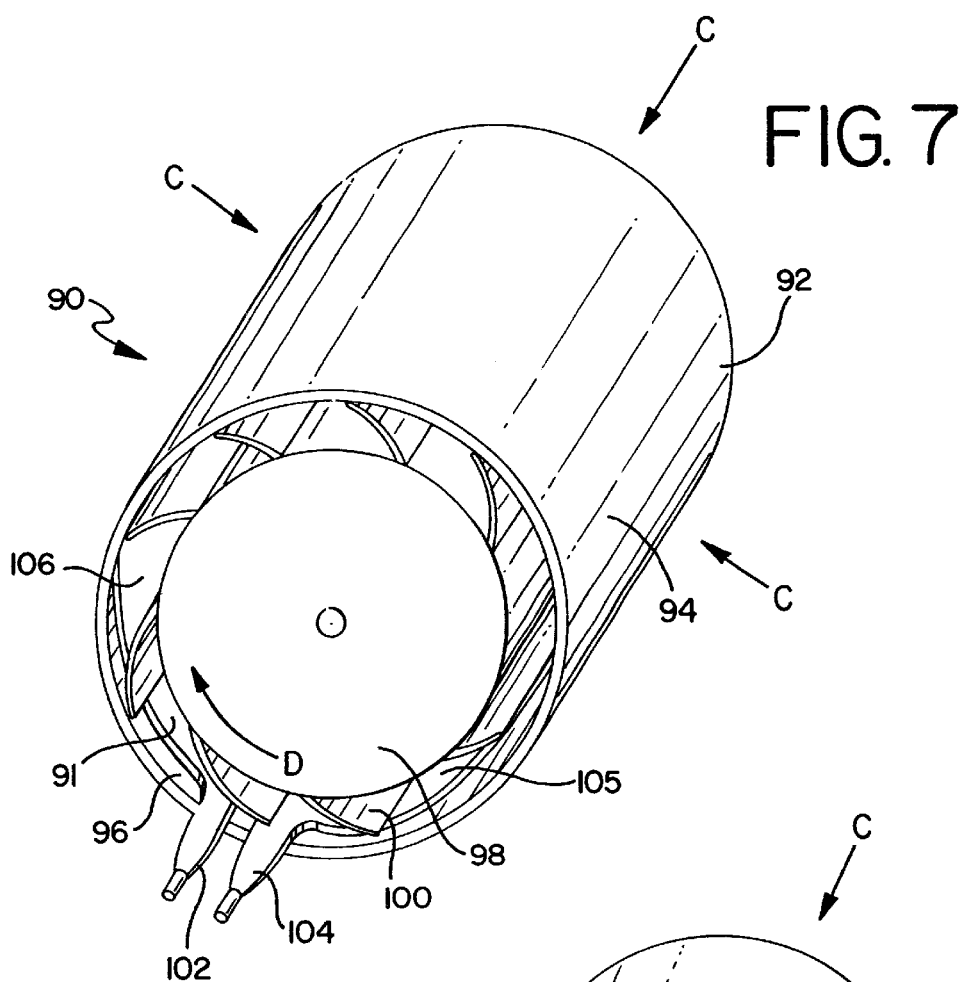
FIG. 7 is a perspective view of a fifth embodiment of the present invention that utilizes an inner cylinder having flexible vanes disposed within a hollow outer cylinder to move a fluid through a thin chamber being exposed to sterilizing radiation.

FIG. 7 shows a device 90 wherein a belt chamber 91 is positioned within a radiation permeable form, in the form of a hollow, radiation permeable outer cylinder 92 having an outer surface 94 and an inner surface 96. An inner cylinder 98 is concentrically disposed within the outer cylinder 92. A motor (not shown) rotatably drives the inner cylinder 98. The inner cylinder 98 has a plurality of flexible vanes 100 attached thereto and angled in a direction opposite that of the direction of rotation (as indicated by arrow D in FIG. 7). The belt chamber 91 is disposed between, and in contact with, the inner surface 96 of the outer cylinder 92 and the inner cylinder 98. Preferably, the belt chamber 91 is designed to be disposable.

A pump (not shown) or other means delivers a fluid supply to the belt chamber 91 that is introduced through a fluid inlet 102 and exits out of the belt chamber through a fluid outlet 104. As the fluid is introduced into the belt chamber 91, the inner cylinder 98 rotates and the flexible vanes 100 provide a squeegee-like mechanism against an inner surface 105 of the belt chamber 91 to move the fluid through the belt chamber 91 in discrete thin packets of fluid 106 defined by a pair of vanes 100. This squeegee-like action helps eliminate or significantly minimize the formation of a typical fluid flow velocity profile within the belt chamber, and, therefore, eliminates or reduces the effects that channel flow velocity profiles have on residence times of the fluid. The fluid is exposed to sterilizing radiation (indicated by arrows C) passing through the outer cylinder 92 as the fluid moves through the belt chamber 22. The sterilizing radiation is provided by a radiation source (not shown).

Figure 8:
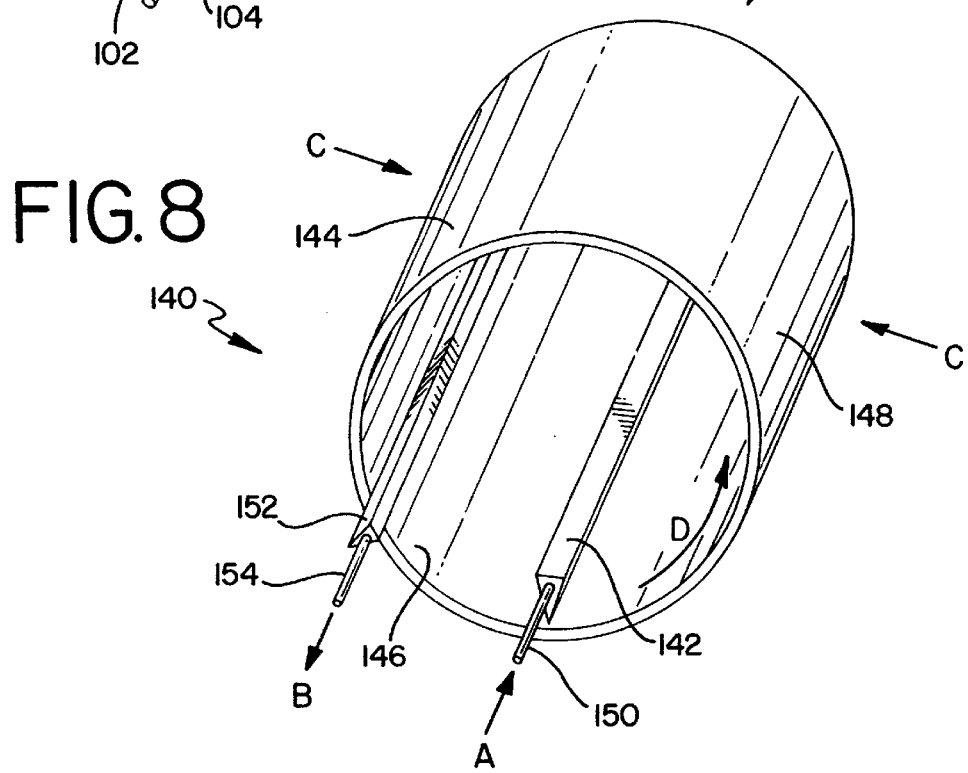
FIG. 8 is a perspective view of a sixth embodiment of the present invention that deposits a thin film of fluid on an inner surface of a rotating cylinder to move the thin film while being exposed to sterilizing radiation.

In another embodiment shown in FIG. 8, a thin film fluid irradiation device 140 is provided in a cylindrical form without the use of a belt chamber. In this configuration, a stationary elongated V-shaped depositor 142 is disposed within a radiation permeable form, in the form of a rotating hollow cylinder 144 having an inner surface 146 and an outer surface 148. The cylinder 144 is highly transparent to the particular radiation being utilized to sterilize the fluid. A motor (not shown) rotatably drives the cylinder 144. A fluid inlet 150 is in fluid communication with the depositor 142. The depositor 142 has a fluid opening (not shown) at its base that deposits a thin film of fluid on the inner surface 146 of the cylinder 144 as the cylinder 144 rotates in a direction indicated by arrow D in FIG. 8. The thin film is carried on the inner surface 146 of the rotating cylinder 144 until it reaches a stationary squeegee collector 152 in contact with the inner surface 146 of the cylinder 144.

A radiation source (not shown) adjacent to the outside surface 148 of the cylinder 144 provides sterilizing radiation (indicated by arrows C in FIG. 8) and irradiates the thin film of fluid carried on the inner surface 146 of the cylinder 144. The squeegee collector 152 is in fluid communication with a fluid outlet 154. The irradiated fluid exits the device 150 through the fluid outlet 154. One or more pumps deliver a fluid supply to the fluid inlet 150 and from the fluid outlet 154.

Figure 9:
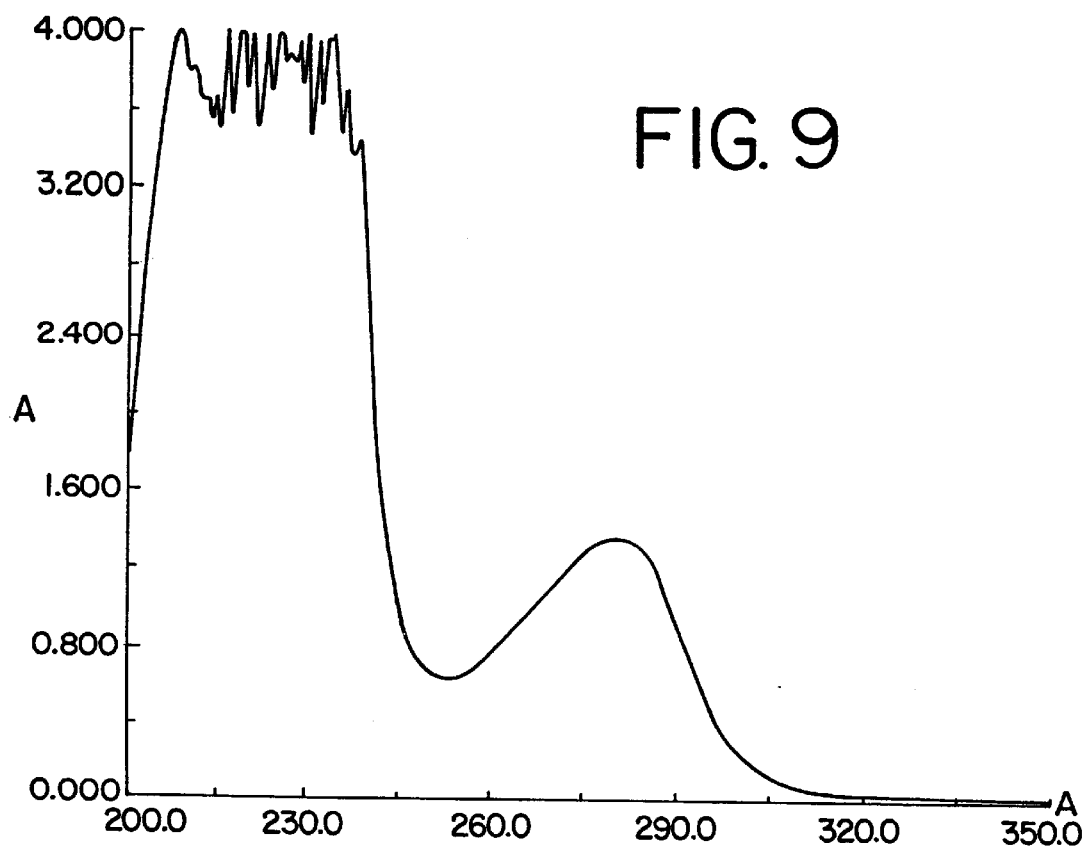
FIG. 9 is a graph depicting ultraviolet radiation absorptivity of human plasma at 42-fold dilution between 200 nm and 350 nm UV wavelengths.

The radiation source utilized for sterilizing the fluid is preferably an ultraviolet (UV) radiation source, such as a UV laser or pulse laser. However, gamma or electron beam (beta) radiation can also be used. The type of sterilizing radiation may vary according to the particular fluid being sterilized. All of these types of sterilizing radiation have been found to be effective against a broad range of pathogens. The graph depicted in FIG. 9 shows the absorptivity of human plasma at 42-fold dilution over a range of wavelengths. Preferably, UV radiation having a wavelength between 240 nm and 250 nm is used for treating human plasma. The plate 32, the outer cylinder 92, and the cylinder 144 are all preferably made of fused quartz, which is substantially transparent to UV radiation.

The belt chambers 22, 72, and 91 are preferably made of a material having the following properties: low modulus, high flexibility, high transparency for the type of radiation being utilized, tough and abrasion resistant, radiation resistant for the doses accumulated in one treatment step, clean and sterilizable by common methods. The material must also be capable of being formed into a belt geometry. Furthermore, since this treatment device and method involves biological fluids containing pathogens, the belt chambers 22, 72, and 91 can also be designed to be disposable. Some suitable materials include low density polyethylene (LDPE), tetrafluoro ethylene hexafluoropropylene copolymers sold under the tradename FEP® by DuPont, silicone rubber, aliphatic polyurethane rubber and tetrafluoroethylene hexafluoropropylene vinylidine fluoride terpolymers sold under the tradename VITON® by DuPont and THV® by Dyneon.

The material for the flexible vanes in all of the aforementioned embodiments is preferably an elastomeric material having suitable rigidity and flexibility for interacting with the belt chambers Suitable materials for the flexible vanes include: polyether ester elastomers sold under the trade name HYTREL® by DuPont, natural rubber, synthetic polyisoprene, olefinic thermoplastic elastomers sold under the trade name SANTOPRENE®by Advanced Elastomer Systems, thermoplastic polyamide elastomers sold under the trade name PEBAX® by Elf Atochem, thermoplastic polyester elastomers sold under the trade name ECDEL® by Eastman Chemical, and styrene based thermoplastic block copolymers sold under the trade name KRATON® by Shell Chemical. Lubricating substances, such as silicone oil can be compounded into the elastomer to insure long term lubrication and low abrasion of the belt chambers.

Figure 10:
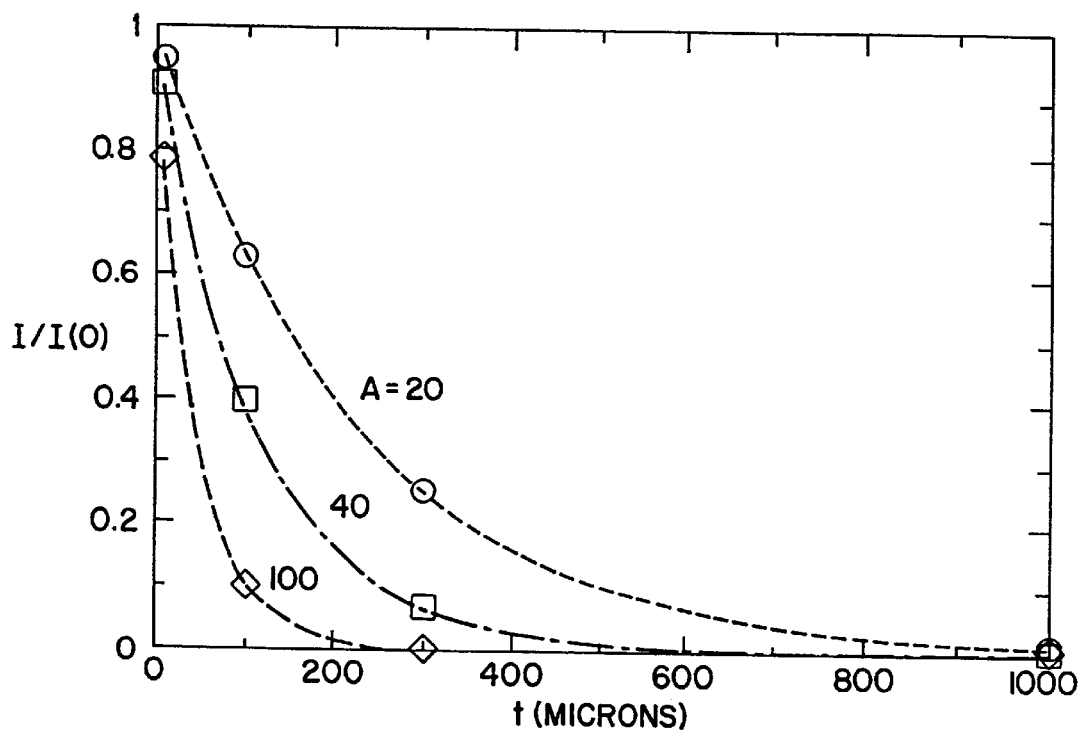
FIG. 10 is a graph depicting light intensity as a function of penetration depth at absorbances of 20, 40 and 100.

The penetration of sterilizing radiation into many biological fluids is quite shallow. FIG. 10 shows a graph depicting light intensity as a function of penetration depth at absorbances of 20, 40 and 100. Ultraviolet (UV) radiation at 250 nm wavelength loses half of the intensity in human plasma at about a 75 micron (about 3 mils) penetration. This can lead to non-uniform dose distribution of the radiation within the fluid, especially in larger size fluid paths. The thin film fluid path within the belt chamber 22, 72, 91, and the cylinder 144 of the device 150 substantially minimizes this effect, and, therefore, provides for more uniform radiation exposure of the fluid. The bottom surface 30 of the belt chamber 22, the bottom surface 76 of the narrow belt chamber 72, and the inner surface 105 of the belt chamber 91 can also be made of material containing a UV reflective material, such as a metal oxide, to further aid in providing uniform radiation exposure of the fluid. The reflective material may also be printed on these surfaces. Preferably, the coating is magnesium oxide or titanium oxide.

All of the embodiments utilize a "conveying" mechanism on the fluid, such as the squeegee-like mechanism, rather than a pressurized forced fluid flow. This eliminates the development of a typical velocity profile within the belt chambers 22, 72, 91, and the cylinder 144 of the device 140. In a typical channel flow velocity profile, the fluid at the center of the channel is traveling at maximum velocity and the fluid close to the channel wall remains nearly stationary. Therefore, the residence time is the shortest for the maximum velocity at the center and increases for successive portions of the flow profile. In a pressurized flow system, the flow volume near the channel walls runs the risk of overexposure to the radiation. Thus, the "conveying" mechanisms of the present invention eliminate or greatly reduce the effects that channel flow velocity profiles have on residence times of the fluid. These mechanisms also eliminate very high pressure drops and shear stresses caused by pressurized flow through narrow channels. This pressure and stress can cause damage to proteins in the fluid, which is undesirable.

There are numerous advantages of providing a disposable and separately sterilizable belt chamber. The belt chamber of the present invention is isolated from the conveying mechanism. The conveying mechanism never comes into contact with the potentially viral contaminated biological fluids. Hence, the treatment apparatus requires minimum disassembly, cleaning and resterilization between production runs. Furthermore, all of the devices described herein can be incorporated into a closed system, thus minimizing fluid contact with air and minimizing fluid degradation. Finally, since the functions of the device are isolated in different components of the device, it is much easier to establish validation, efficacy, reproducibility and reliability of the device.

While the specific embodiments have been illustrated and described, numerous modifications come to mind without significantly departing from the spirit of the invention and the scope of protection is only limited by the scope of the accompanying claims.

What is claimed is:

1. A device for inactivating pathogens in a fluid, the device comprising:
   a radiation permeable chamber having a fluid inlet, a fluid outlet, a first surface and a second surface, the fluid inlet and the fluid outlet in fluid communication with a fluid flow;
   a rigid radiation permeable form disposed adjacent to and in contact with the first surface of the chamber, and a plurality of flexible vanes disposed adjacent to and in contact with the second surface of the chamber, the flexible vanes exerting a force against the rigid-radiation permeable form and being movable with respect to the chamber in a direction of the fluid flow so that the fluid is moved within the chamber when the vanes move; and a radiation source disposed at a fixed distance from the chamber that provides irradiation of the fluid moving through the chamber.

2. The device of claim 1, wherein the radiation source is an ultraviolet laser.

3. The device of claim 2, wherein the ultraviolet laser is a pulse laser.

4. The device of claim 1, wherein the chamber is flexible.

5. The device of claim 4, wherein the chamber is of a relatively flat shape.

6. The device of claim 4, wherein the chamber is removable and disposable.

7. The device of claim 1, wherein the flexible vanes move the fluid within the flexible chamber in discrete packets of fluid formed between a pair of immediately adjacent vanes.

8. The device of claim 1, wherein the flexible vanes are disposed on a conveyor-type belt mechanically connected to a drive mechanism.

9. The device of claim 1, wherein the rigid radiation permeable form is a plate.

10. The device of claim 9, wherein the plate is a fused quartz plate.

11. The device of claim 1, wherein the radiation permeable chamber is a rotatable rigid hollow cylinder having an inner surface, the first surface of the chamber is the inner surface, and further comprising a motor mechanically connected to the chamber, wherein the fluid enters the cylinder through the fluid inlet and is deposited on the inner surface of the cylinder and forms a film carried by the inner surface of the cylinder to the fluid outlet as the cylinder rotates.

12. A device for inactivating pathogens in a fluid, the device comprising:
   a radiation permeable chamber having a fluid inlet, a fluid outlet, a first surface and a second surface, the fluid inlet and the fluid outlet in fluid communication with a fluid flow;
   a rigid radiation permeable form disposed adjacent to and in contact with the first surface of the chamber, and a plurality of rotatable rigid cylinders each having an axis of rotation and disposed adjacent to and in contact with the second surface of the chamber, the rigid cylinders exerting a force against the rigid radiation permeable form and being movable with respect to the chamber in a direction of the fluid flow so that the fluid is moved within the chamber when the cylinders move and rotate; and
   a radiation source disposed at a fixed distance from the chamber that provides irradiation of the fluid moving through the chamber.

13. The device of claim 12, wherein the rigid cylinders move the fluid within the flexible chamber in discrete packets of fluid formed between a pair of immediately adjacent cylinders.

14. The device of claim 12, wherein the rigid cylinders are rotatably disposed on a conveyor-type belt mechanically connected to a drive mechanism.

15. The device of claim 12, wherein the rigid radiation permeable form is a plate.

16. The device of claim 15, wherein the plate is a fused quartz plate.

17. A device for inactivating pathogens in a fluid, the device comprising:

a radiation permeable chamber having a fluid inlet, a fluid outlet, a first surface and a second surface, the fluid inlet and the fluid outlet in fluid communication with a fluid flow;

a rigid radiation permeable form disposed adjacent to and in contact with the first surface of the chamber, and a plurality of rollers having spirally configured flexible vanes disposed thereon, the rollers disposed adjacent to the second surface of the chamber such that the flexible vanes contact the second surface of the chamber and exert a force against the rigid radiation permeable form, the rollers being rotatable in a direction of the fluid flow so that the fluid is moved within the chamber by the vanes when the rollers rotate; and a radiation source disposed at a fixed distance from the chamber that provides irradiation of the fluid moving through the chamber.

18. The device of claim 17, wherein the rollers are mechanically connected to a drive mechanism driven by a motor.

19. A device for inactivating pathogens in a fluid, the device comprising:

a radiation permeable chamber having a fluid inlet, a fluid outlet, a first surface and a second surface, the fluid inlet and the fluid outlet in fluid communication with a fluid flow;

a rigid radiation permeable form disposed adjacent to and in contact with the first surface of the chamber, and a roller having spirally configured flexible vanes disposed thereon, the roller being disposed parallel to the fluid flow and adjacent to the second surface of the chamber such that the flexible vanes contact the second surface of the chamber and exert a force against the rigid radiation permeable form, the roller being rotatable in a direction transverse to the fluid flow so that the fluid is moved within the chamber by the vanes when the roller rotates; and a radiation source disposed at a fixed distance from the chamber that provides irradiation of the fluid moving through the chamber.

20. The device of claim 14, wherein the roller is mechanically connected to a drive mechanism driven by a motor.

21. A device for inactivating pathogens in a fluid, the device comprising:

a radiation permeable chamber having a fluid inlet, a fluid outlet, a first surface and a second surface, the fluid inlet and the fluid outlet in fluid communication with a fluid flow;

a rigid radiation permeable outer cylinder having an inner surface, and an inner rotatable cylinder having a plurality of flexible vanes, the inner cylinder concentrically disposed within the outer cylinder such that the chamber is concentrically disposed between the outer cylinder and the inner cylinder and the plurality of flexible vanes are in contact with the chamber, the plurality of flexible vanes exerting a force against the inner surface of the outer cylinder such that when the inner cylinder rotates, the vanes move the fluid within the chamber; and a radiation source disposed at a fixed distance from the chamber that provides irradiation of the fluid moving through the chamber.

22. A device for inactivating pathogens in a fluid, the device comprising:

a radiation permeable chamber having a fluid inlet, a fluid outlet, a first surface and a second surface, the fluid inlet and the fluid outlet in fluid communication with a fluid flow;

a rigid radiation permeable form disposed in contact with the first surface of the chamber;

a plurality of movable forms disposed in contact with the second surface of the chamber and exerting a force against the radiation permeable form such that the fluid is moved through the chamber as the movable forms move with respect to the chamber; and a radiation source disposed at a fixed distance from the chamber that provides irradiation of the fluid moving through the chamber.

23. The device of claim 22, wherein the radiation permeable form is a flat plate.

24. The device of claim 22, wherein the radiation permeable form is a hollow cylinder.

25. The device of claim 22, wherein the radiation source provides sterilizing ultraviolet radiation.

26. The device of claim 25, wherein the sterilizing ultraviolet radiation has a wavelength between approximately 240 nm and 260 nm.

27. A method for inactivating pathogens in fluids with sterilizing radiation in a continuous flow arrangement comprising the steps of:

forming a fluid path within a radiation permeable chamber for a fluid in a continuous flow;

conveying the fluid through the chamber in a manner that substantially eliminates the development of a velocity profile in the fluid; and radiating the fluid within the chamber.

* * * * *